(12) United States Patent
Wang

(10) Patent No.: US 8,043,367 B2
(45) Date of Patent: Oct. 25, 2011

(54) STENTS FORMED FROM POLYMER-BIOCERAMIC COMPOSITE WITH RADIOPAQUE BIOCERAMIC PARTICLES

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/070,961

(22) Filed: Mar. 24, 2011

(65) Prior Publication Data
US 2011/0172758 A1 Jul. 14, 2011

Related U.S. Application Data

(62) Division of application No. 11/968,600, filed on Jan. 2, 2008, now Pat. No. 7,935,143.

(51) Int. Cl.
*A61F 2/06* (2006.01)
*B05D 3/00* (2006.01)

(52) U.S. Cl. ............. 623/1.42; 623/1.34; 623/1.43; 427/2.24; 427/2.25

(58) Field of Classification Search ............. 623/1.34, 623/1.42, 23.56, 23.58, 23.6, 23.76; 604/103.1, 604/529; 606/912; 523/113, 114
See application file for complete search history.

(56) References Cited

U.S. PATENT DOCUMENTS

| | | | |
|---|---|---|---|
| 4,619,655 A * | 10/1986 | Hanker et al. ............. | 623/23.61 |
| 6,283,997 B1 | 9/2001 | Garg et al. | |
| 6,395,029 B1 | 5/2002 | Levy | |
| 6,585,755 B2 | 7/2003 | Jackson et al. | |
| 6,599,558 B1 * | 7/2003 | Al-Lamee et al. ............. | 427/2.24 |
| 6,730,120 B2 | 5/2004 | Berg et al. | |
| 6,926,733 B2 | 8/2005 | Stinson | |
| 7,541,049 B1 | 6/2009 | Tormala et al. | |
| 7,824,601 B1 | 11/2010 | Stankus et al. | |
| 7,935,143 B2 | 5/2011 | Wang | |
| 2003/0104028 A1 | 6/2003 | Hossainy | |
| 2004/0186551 A1 | 9/2004 | Kao et al. | |
| 2005/0064224 A1 | 3/2005 | Bavaro et al. | |
| 2005/0209680 A1 | 9/2005 | Gale et al. | |
| 2005/0261479 A1 * | 11/2005 | Hoffmann et al. ............. | 530/353 |
| 2007/0282426 A1 | 12/2007 | Wang et al. | |
| 2007/0282431 A1 | 12/2007 | Gale et al. | |
| 2008/0009939 A1 | 1/2008 | Gueriguian et al. | |
| 2008/0058919 A1 | 3/2008 | Kramer-Brown et al. | |

(Continued)

FOREIGN PATENT DOCUMENTS
EP 1721625 A2 * 11/2006
(Continued)

OTHER PUBLICATIONS

U.S. Appl. No. 11/818,304, filed Jun. 13, 2007, Gale et al.
(Continued)

*Primary Examiner* — Thomas J Sweet
*Assistant Examiner* — Yashita Sharma
(74) *Attorney, Agent, or Firm* — Squire Sanders & Dempsey, (US) LLP

(57) ABSTRACT

Implantable medical devices fabricated at least in part of a polymer-bioceramic composite having bioceramic particles with radiopaque functional groups grafted to a surface of the bioceramic particles are disclosed. Implantable medical devices fabricated at least in part of a radiopaque material having bioceramic particles with polymer chains grafted onto a surface of the bioceramic particles, the radiopaque functional groups being chemically bonded to the grafted polymer chains, are disclosed.

8 Claims, 8 Drawing Sheets

U.S. PATENT DOCUMENTS

| | | | |
|---|---|---|---|
| 2008/0081063 | A1 | 4/2008 | Wang et al. |
| 2008/0086199 | A1 | 4/2008 | Dave et al. |
| 2008/0269874 | A1 | 10/2008 | Wang et al. |
| 2009/0149940 | A1 | 6/2009 | Wang et al. |

FOREIGN PATENT DOCUMENTS

| | | |
|---|---|---|
| WO | WO 2005/056097 | 6/2005 |
| WO | WO 2007/143698 | 12/2007 |

OTHER PUBLICATIONS

U.S. Appl. No. 11/823,931, filed Jun. 29, 2007, Wang et al.

International Search Report for PCT/US2008/086426, mailed Mar. 22, 2010, 6 pgs.

Barrett et al. "Endovascular Embolization of Varicoceles: Resorption of Tungsten Coils in the Spermatic Vein", Cardiovasc. Intervent. Radiol. 23, pp. 457-459 (2000).

Butler et al., "In vivo degradation of tungsten embolisation coils", The British J. of Radiology 73, pp. 601-603 (2000).

Chen et al., "Toughening of Polypropylene-Ethylene Copolymer with Nanosized $CaCo_3$ and Styrene-Butadiene-Styrene", J. of Applied Polymer Science 94, pp. 796-802 (2004).

Hong et al., "Nano-composite of poly(L-lactide) and surface grafted hydroxyapatite: Mechanical properties and biocompatibility", Biomaterials 26, pp. 6296-6304 (2005).

Neilsen, Mechanical Properties of Polymers and Composites, $2^{nd}$ ed. pp. 384-385 (1994).

Nottelet, "Synthesis of an X-ray opaque biodegradable copolyester by chemical modification of poly($\epsilon$-caprolactone)", Science Direct, Biomaterilas 27, pp. 4948-4954 (2006).

Peuster et al., "Degradation of tungsten coils implanted into the subclavian artery of New Zealand white rabbits is not associated with local or systemic toxicity", Biomaterials 24 pp. 393-399 (2003).

Thamaraiselvi et al., "Biological Evaluation of Bioceramic Materials—A Review", Trends Biomater. Artif. Organs, vol. 18, pp. 9-17 (2004).

Wei Li "Dissolution of tungsten coils leads to device failure after transcatheter embolisation of pathologic vessels", Heart 85, pp. 703-704 (2001).

Weill et al., ""Corrosion" of Tungsten Spirals. A disturbing Finding", Interventional Neuroradiology 4 pp. 337-340 (1998).

Zhang, "Processing and Properties of porous poly(L-lactide)/bioactive glass composites", Biomaterials 25, pp. 2489-2500 (2004).

\* cited by examiner

STENTS FORMED FROM POLYMER-BIOCERAMIC COMPOSITE WITH RADIOPAQUE BIOCERAMIC PARTICLES

CROSS-REFERENCE TO RELATED APPLICATIONS

This application is a divisional of application Ser. No. 11/968,600, filed Jan. 2, 2008, now U.S. Pat. No. 7,935,143 which is incorporated herein by reference.

BACKGROUND OF THE INVENTION

1. Field of the Invention

This invention relates to implantable medical devices and methods of fabricating implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. The stent may be visualized during delivery and deployment using X-Ray fluoroscopy if it contains radiopaque materials.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

In addition to meeting the mechanical requirements described above, it is desirable for a stent to be sufficiently radiopaque to be fluoroscopically visible under x-rays. Accurate stent placement is facilitated by real time visualization of the delivery of a stent. A cardiologist or interventional radiologist can track the delivery catheter through the patient's vasculature and precisely place the stent at the site of a lesion. This is typically accomplished by fluoroscopy or similar x-ray visualization procedures. For a stent to be fluoroscopically visible it must be more absorptive of x-rays than the surrounding tissue. Radiopaque materials in a stent may allow for its direct visualization.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with polymeric implantable medical devices, such as stents, include insufficient toughness, slow degradation rate, and limited shelf life due to physical aging and stress relaxation. Another problem with polymeric stents is that polymers tend to be radiolucent, and thus cannot be visualized with X-ray fluoroscopy.

SUMMARY OF THE INVENTION

Various embodiments of the present invention include a stent formed at least in part from a bioceramic/polymer composite, the composite having a plurality of bioceramic particles dispersed within a matrix polymer, wherein the bioceramic particles comprise radiopaque functional groups grafted to a surface of the bioceramic particles, wherein the radiopaque functional groups allow the stent to be fluoroscopically visible.

Further embodiments of the present invention include a stent fabricated at least in part from a radiopaque material comprising bioceramic particles having polymer chains grafted onto a surface of the bioceramic particles, wherein radiopaque functional groups are chemically bonded to the grafted polymer chains.

DETAILED DESCRIPTION OF THE INVENTION

Embodiments of the present invention may be applied to stents and, more generally, to implantable medical devices such as, but not limited to, self-expandable stents, balloon-expandable stents, stent-grafts, vascular grafts, or generally, tubular implantable medical devices.

An implantable medical device can be designed for the localized delivery of a therapeutic agent. A medicated implantable medical device may be constructed by coating the device with a coating material containing a therapeutic agent. The substrate of the device may also contain a therapeutic agent.

Figure 1:
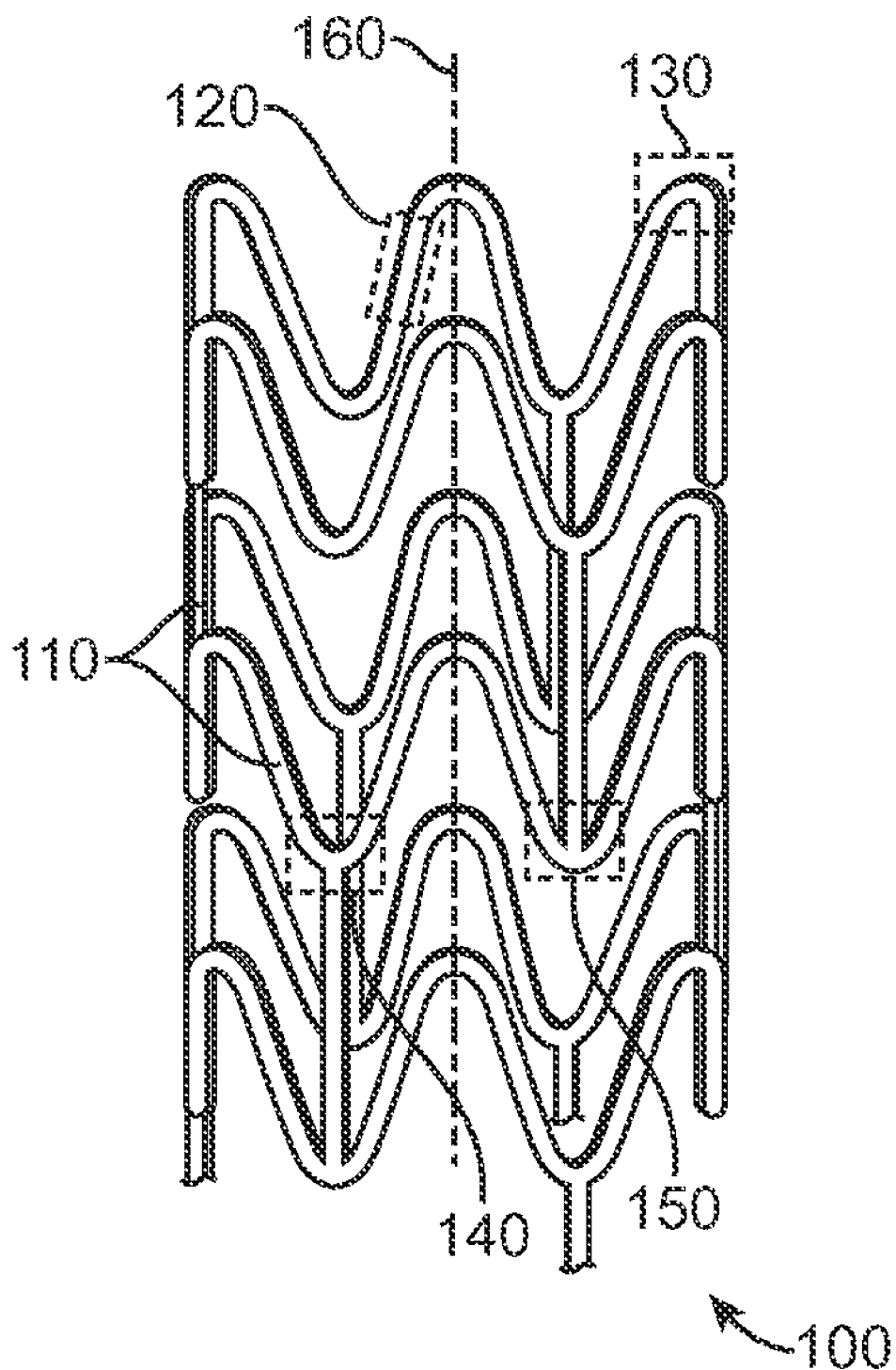
FIG. 1 depicts a three-dimensional view of a stent.

FIG. 1 depicts a three-dimensional view of stent 100. In some embodiments, a stent may include a pattern or network of interconnecting structural elements 110. Stent 100 has a cylindrical axis 160 and may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

The geometry or shape of an implantable medical device may vary throughout its structure to allow radial expansion and compression. A pattern may include portions of structural elements or struts that are straight or relatively straight, an example being a portion 120. In addition, patterns may include structural elements or struts that include curved or bent portions such as portions 130, 140, and 150.

An implantable medical device can also be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

There are several characteristics that are important for implantable medical devices, such as stents, including high radial strength, good fracture toughness, fast degradation, and radiopacity. Some polymers that may be suitable for use in implantable medical devices have potential shortcomings with respect to one or more of these characteristics, in particular, fracture toughness. Some crystalline or semi-crystalline polymers that are glassy or have a Tg above body temperature are particularly attractive as stent materials due to their strength and stiffness. The toughness of such polymers can be lower than desired, in particular, for use in stent applications. For example, polymers such as PLLA are stiff and strong, but tend to be brittle under physiological conditions. Physiological conditions refer to conditions that an implant is exposed to within a human body. Physiological conditions include, but are limited to, human body temperature, approximately 37° C.

These polymers can exhibit a brittle fracture mechanism at these conditions in which there is little or no plastic deformation prior to failure. As a result, a stent fabricated from such polymers can have insufficient toughness for the range of use of a stent. In particular, certain regions of an implantable medical device, such as a stent, experience a high degree of stress and strain when the device is under stress during use. For example, when a stent is crimped and deployed, curved or bending regions such as portions 130, 140, and 150 can have highly concentrated strain which can lead to fracture.

Furthermore, some biodegradable polymers have a degradation rate that is slower than desired for certain stent treatments. As a result, the degradation time of a stent made from such polymers can be longer than desired. For example, a stent made from a semicrystalline polymer such as PLLA can have a degradation time between about two and three years. In some treatment situations, a shorter degradation time is desirable, for example, less than 6 months or a year.

Additionally, polymers generally do not possess sufficient radiographic density to be easily imaged by fluoroscopy. Since a device such as a stent also has specific mechanical requirements, it is important that rendering a polymeric stent sufficiently radiopaque for imaging does not significantly impact its mechanical behavior.

Embodiments of the present invention address shortcomings of polymers for use in implantable medical devices with respect to toughness, degradation rate, and radiopacity. Various embodiments of the present invention include a stent formed partially or completely of a bioceramic/polymer composite. The composite includes a plurality of radiopaque bioceramic particles dispersed within a polymer. The bioceramic particles are radiopaque due to molecules having radiopaque functional group(s) that are grafted to the ceramic surface of the bioceramic particles. The radiopaque functional groups can be formed from iodine-substituted compounds including, but not limited to, triiodobenzoyl chloride, triiodobenzoic acid, or combinations thereof. In such embodiments, the radiopaque functional groups allow the stent to be fluoroscopically visible.

In the certain embodiments of the invention, the bioceramic particles increase the fracture toughness and modulus of the composite of the device. In general, the higher the fracture toughness, the more resistant a material is to the propagation of cracks. In some embodiments, the bioceramic particles may be dispersed within a matrix polymer that is brittle at physiological conditions. In particular, such a polymer can have a Tg above body temperature.

It is believed that the bioceramic particles can increase fracture toughness by reducing the concentration of strain by dispersing the strain over a larger volume of the material. Particles can absorb energy due to applied stress and disperse energy about a larger volume in the bioceramic/polymer composite. Therefore, rather than being highly concentrated the stress and strain in a device fabricated from a bioceramic composite is divided into many small interactions involving numerous individual particles. When a crack is initiated in the material and starts traveling through the composite, the crack breaks up into finer and finer cracks due to interaction with the particles. Thus, the particles tend to dissipate the energy imparted to the device by the applied stress.

It is advantageous to use nanoparticles to increase the toughness of the polymer. It has been shown that the fracture toughness of a polymeric material can be improved by using nanoparticles as a discrete or reinforcing phase in a composite. J. of Applied Polymer Science, 94 (2004) 796-802.

Figure 2:
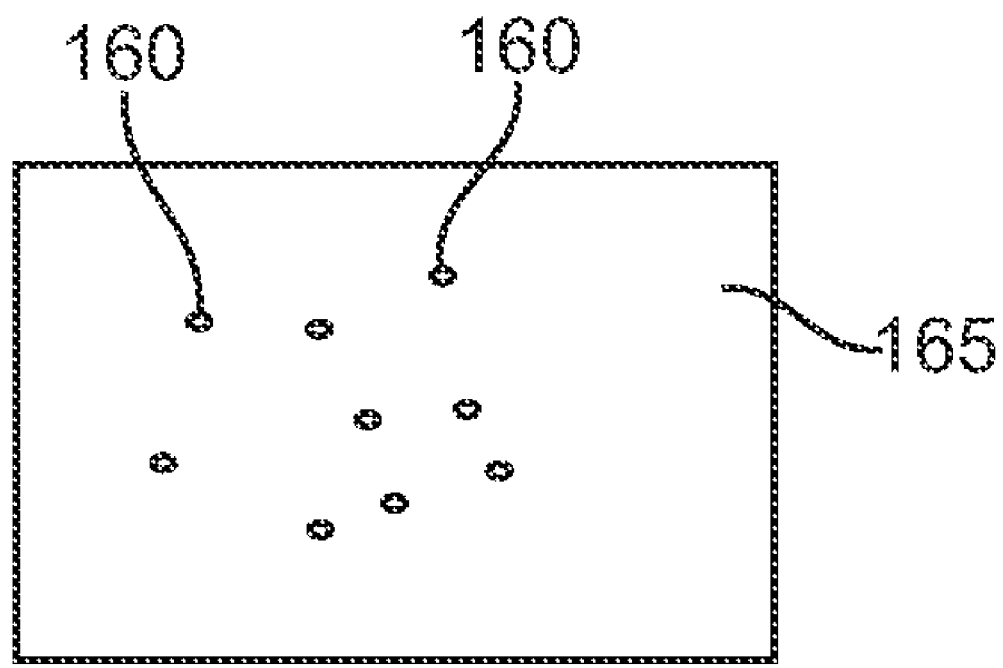
FIG. 2 depicts a schematic illustration of the microstructure of a composite showing bioceramic particles dispersed throughout a polymer matrix.

As described in detail below, the composite can be used in various ways in the fabrication of device, such as a stent. In some embodiments, a stent body can be formed from the composite, such as that depicted in FIG. 1. In other embodiments, the composite can be a layer of a structural element of a stent body. In still other embodiments, the composite can be a coating over a stent body. FIG. 2 depicts a schematic illustration of the microstructure of a composite showing bioceramic particles 160 dispersed throughout a polymer matrix 165.

In some embodiments, a stent can be formed at least in part from a bioceramic/polymer composite that include bioceramic particles with radiopaque functional groups that are grafted to a ceramic surface of the bioceramic particles. In such embodiments, the radiopaque compounds, such as ion-substituted compounds, may react with a ceramic surface of a particle to graft the radiopaque compound to the ceramic surface. In such embodiments, the radiopaque compound can react with hydroxyl groups on the ceramic surface. Such compounds may react by an esterification reaction of hydroxyl groups at the ceramic surface.

Figure 3:
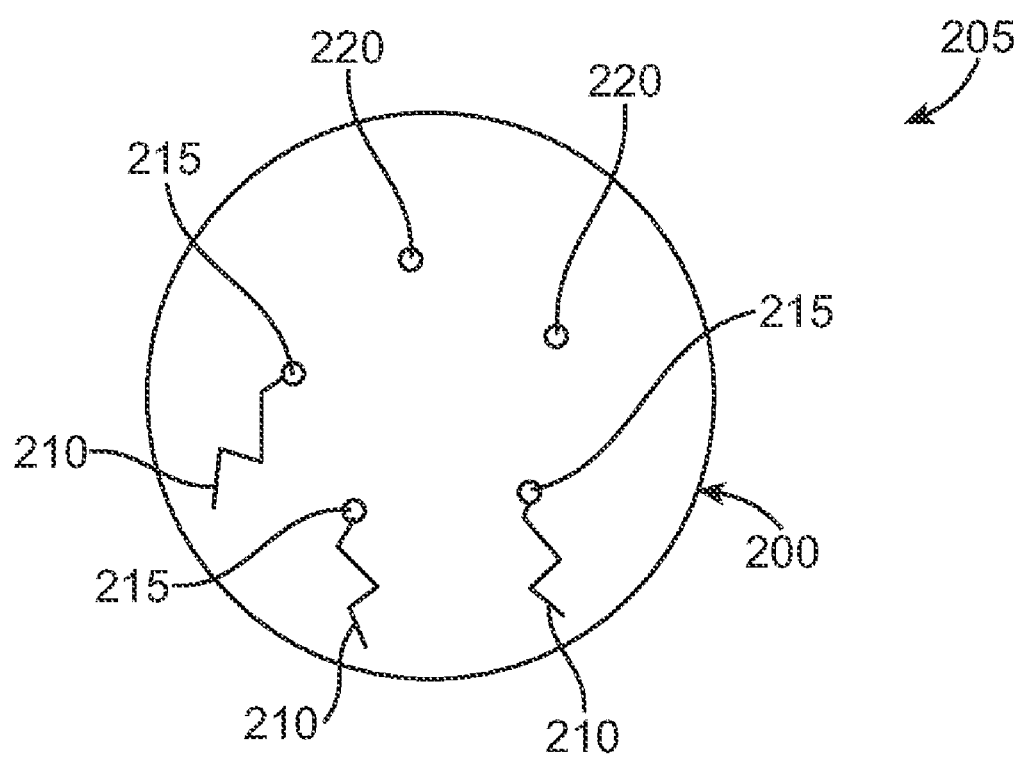
FIG. 3 depicts a schematic illustration of an embodiment of a radiopaque bioceramic particle embedded in a matrix polymer.

FIG. 3 depicts a schematic illustration of an embodiment of a bioceramic particle 200 embedded in a matrix polymer 205. Polymer chains of the matrix polymer are not shown for the sake of clarity. Particle 200 has radiopaque functional groups 210 grafted or bonded to a surface of particle 200 at sites 215. Particle 200 further includes reactive sites 220 with no grafted radiopaque groups.

Bioceramic particles with grafted radiopaque functional groups can be made by disposing bioceramic particles in a solvent that includes a radiopaque compound. In an exemplary embodiment, hydroxylapatite particles are disposed in chloroform (solvent) with triethylamine (TEA) and triiodobenzoyl chloride as the radiopaque compound. An esterification reaction occurs between the triiodobenzoyl chloride and the hydroxyl groups of the hydroxylapatite resulting in triiodobenzoyl moieties grafted to the ceramic surface. TEA is used to help neutralize the pH value of the solution. When triisdobenzoyl chloride reacts with the hydroxyl groups of nano bioceramic, it releases HCL.

In another set of embodiments, a stent may be formed at least in part from a bioceramic/polymer composite with bioceramic particles having polymer chains grafted onto the ceramic surface of the bioceramic particles. In such embodiments, radiopaque functional groups are chemically bonded to the grafted polymer chains. In these embodiments, the radiopaque polymer chains may be grafted or bonded to reactive groups, such as hydroxyl groups, on the ceramic surface of the bioceramic particles.

In some embodiments, the composite including bioceramic particles with grafted polymer can be dispersed within a matrix polymer. In such embodiments, the grafted polymers may be miscible with the matrix polymer. In an embodiment, the chemical composition of the grafted polymers may be the same or substantially the same as the matrix polymer. It is believed that such grafted polymers may extend from the surface of the polymers into the polymer matrix and stabilize the particles in the matrix. In other embodiments, a composite be composed primarily or completely of bioceramic particles dispersed within the grafted polymers.

Exemplary grafting polymers include homopolymers such as PLLA, poly(4-hydroxyl butyrate) (PHB), poly(trimethylene carbonate) (PTMC), polydioxanone (PDO), and other crystalline or semi-crystalline hydrolytically degradable polymers. The grafting polymers can also include random, alternating, and block copolymers such as poly(L-lactide-co-glycolide) (PLGA), PLLA-co-PCL, and PLLA-b-PCL. In exemplary embodiments, the grafting polymers can be PLLA, PLGA, and the matrix polymer can be PLLA or PLGA.

In some embodiments, a radiopaque functional group can be bonded to an end of a grafted polymer. In such embodiments, the radiopaque functional group can be bonded to an end of an aliphatic polyester through an esterification reaction, as described in more detail below. In such a reaction, the radiopaque group is substituted for a proton of a hydroxyl end group.

In further embodiments, radiopaque groups can be covalently bonded to the backbone of some aliphatic polyesters. Biomaterials, 27 (2006) 4948-4954. It has been shown that iodine can be added to the backbone of PCL by the removal of a proton of the methylene group in a position of the ester carbonyl. It is believed that such a scheme can be generally applied to aliphatic polyesters having such methylene groups. These include, but are not limited to, PTMC, PHB, and PDO. Exemplary synthesis schemes are provided herein.

Figure 4:
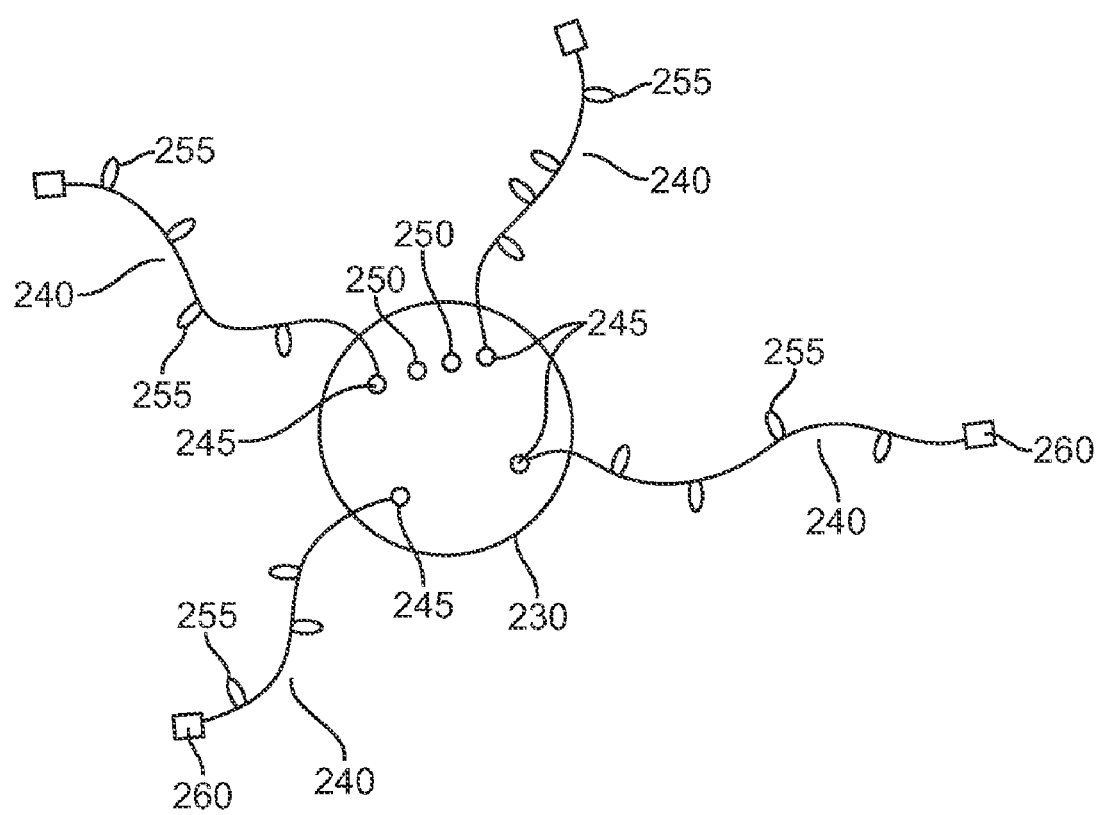
FIG. 4 depicts a schematic illustration of another embodiment of a radiopaque bioceramic particle embedded in a matrix polymer.

FIG. 4 depicts a schematic illustration of another embodiment of a bioceramic particle 230 embedded in a matrix polymer 235. Polymer chains of the matrix polymer are not shown for the sake of clarity. Radiopaque polymer chains 240 with polymer backbones 242 grafted or bonded to a surface of particle 230 at sites 245. Particle 230 further includes reactive sites 250 with no grafted polymer chains. Polymers 240 have radiopaque groups 255 along backbones 242 and radiopaque groups 260 endcapping backbones 242.

In general, good bonding between a continuous phase or matrix and a discrete or reinforcing phase in a composite material facilitates improvement of the mechanical performance of the composite. Thus, in certain embodiments, the grafted polymers can enhance the adhesion of the bioceramic particles to a matrix polymer of a composite.

In general, it is desirable for the bioceramic particles to be uniformly dispersed throughout the biodegradable polymer. For example, a uniform dispersion can result in a uniform increase in toughness and modulus and modification of degradation rate. However, bioceramic particles tend agglomerate or form clusters which make it difficult to disperse the particles within a composite. The presence of larger clusters in the composite tends to result in a decrease in material performance. Such larger clusters can result in the formation of voids in a composite device, which are preferential sites for crack initiation and failure. The agglomeration of bioceramic particles can be reduced by decreasing the surface energy between particles to improve the dispersion of particles in the composite. In some embodiments, the grafted polymer can decrease the surface energy between particles which can decrease agglomeration.

In other embodiments, agglomeration can be reduced by treating particles with a non-reactive surface modifier. Representative examples of non-reactive surface modifiers for treating bioceramic particles include, but are not limited to, stearic acid, polyethylene oxide-b-polypropylene oxide-b-polyethylene oxide (PEO-b-PPO-b-PEO), and polyethylene oxide-b-polylactide.

In further embodiments, a composite can be formed through melt blending a matrix polymer and the radiopaque bioceramic particles. In one embodiment, the matrix polymer and radiopaque bioceramic particles can be melt blended in batch. In other embodiments, the matrix polymer and radiopaque particles can be blended in an extruder. Representative examples of extruders include, but are not limited to, single screw extruders, intermeshing co-rotating and counter-rotating twin-screw extruders and other multiple screw masticating extruders.

As mentioned above, the grafted polymer can reduce or inhibit agglomeration of the particles during the melt blending process. In one embodiment, the composite can be subjected to a shear stress higher than the fracture strength of clusters of the bioceramic particles so that the agglomeration is further reduced. For example, the mixture of matrix polymer and the particles can be processed with a twin-screw extruder or a kneader in such a way that agglomeration of the processed bioceramic particles is reduced.

In certain embodiments, bioceramic particles with grafted polymers with radiopaque groups can be prepared through solution polymerization in suspension. A "suspension" is a mixture in which particles are suspended or dispersed in a fluid. In such embodiments, the bioceramic particles can be dispersed in a solution that includes a fluid with monomers of the grafting polymer dissolved in the fluid, which can also be a solvent for the grafting polymer. The solution can further include a catalyst to facilitate the polymerization reaction. The monomers can be polymerized and at least some of the polymers formed can be bonded or grafted to the surface of the bioceramic particles at the site of the reactive groups.

A radiopaque compound and an initiator can then be added to the suspension to covalently bond the radiopaque compound to ends of the grafted polymers. In an exemplary embodiment, an aliphatic polyester can be the grafting polymer. In such an embodiment, triethylamine as initiator and triiodobenzoyl chloride as the radiopaque compound are added to suspension. An esterification reaction occurs between the triiodobenzoyl chloride and the hydroxyl groups at the end of the grafted polymers resulting in triiodobenzoyl moieties grafted to the ends of the grafted polymers. Additionally, the radiopaque compound can also react with surface hydroxyl groups, as above, to bond directly with the surface.

In some embodiments, the fluid or solvent can then be separated or removed to form a radiopaque bioceramic particle/grafted polymer mixture. In one embodiment, the mixture can be formed through precipitation of the particles in a non-solvent of the grafted polymer. In this embodiment, the solution with the bioceramic particles with grafted polymer can be added to a nonsolvent for the grafted polymer which induces the particles to precipitate with the grafted polymer. In another embodiment, bioceramic particles with grafted polymer can be removed from the solution by evaporating the fluid or solvent from the suspension. For example, the fluid or solvent can be removed in a high vacuum oven.

Additionally or alternatively, radiopaque side groups can then be added to the backbone of the grafted polymer. In an exemplary embodiment, a radiopaque bioceramic/grafted polymer mixture having PCL segments is mixed with lithium diisopropyl amide solution in tetrahydrofuran (THF). Iodine is then added to the solution which results in the formation of iodine side groups along the PCL backbone. The solution is added to a nonsolvent for the grafted polymer to precipitate a radiopaque bioceramic/grafted polymer mixture.

As described in more detail below, the radiopaque bioceramic/grafted polymer mixture may be used in various ways in the fabrication of device, such as a stent. A stent body can be formed by melt blending the mixture with a matrix polymer. The mixture or a blend of the mixture and a matrix polymer can be used as a layer of a structural element of a stent body or a coating over a stent body. In some embodiments, the molecular weight of the grafted polymer can be from 2 kD to 50 kD. In other embodiments, the molecular weight can be less than 2 kD or greater than 50 kD.

As mentioned above the radiopaque particles described herein can be used in various ways in the fabrication of device, such as a stent. In one set of embodiments, a stent body can be formed from the composite including the radiopaque bioceramic particles. In a second set of embodiments, a stent scaffolding or structural element of a stent scaffolding can have a radiopaque layer including the radiopaque bioceramic particles. In a third set of embodiments, a stent body or scaffolding can have a coating that includes the radiopaque bioceramic particles.

In the first set of embodiments, a stent body or scaffolding, such as that depicted in FIG. 1 can be formed from a composite including the radiopaque bioceramic particles blended or mixed with a matrix polymer. In such embodiments, the radiopaque bioceramic particles can be mixed or blended with a matrix polymer, for example, with an extruder as described above. A tube made from the composite can be formed by an extrusion process.

In general, extrusion refers to the process of conveying a polymer through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the final tube product. A stent pattern may then be cut into the composite tube with a process such as laser machining to form a composite stent body or scaffolding. In some embodiments, the tube may be radially expanded, prior to cutting, to improve the radial strength of the tube. The tube may be radially expanded by method such as blow molding. The stent pattern can be cut into the tube in its expanded state.

In such embodiments, the matrix polymer can be a semicrystalline polymer having a Tg above physiological temperature. The grafted polymers of radiopaque bioceramic particles may be miscible with such matrix polymer, have the same or similar chemical composition, or both. In an exemplary embodiment, the matrix polymer is PLLA and the grafted polymer chains are PLLA. In another exemplary embodiment, the matrix polymer is PLGA and the grafted polymer chains are PLGA.

The composite can have a sufficient amount of radiopaque particles to make the stent fluoroscopically visible. The amount of radiopaque material can be adjusted to obtain a desired degree of radiopacity. In exemplary embodiments, the bioceramic particles may be less than 5%, 5-10%, 10-20%, or greater than 20% by volume of the composite. Although bioceramic particles improve toughness at low concentrations, at high enough concentration, the mechanical properties of the polymer may be adversely affected. Thus, the concentration of bioceramic particles can be limited so the mechanical properties of the stent body are not adversely affected.

In the second set of embodiments, a stent can include a stent body or scaffolding having a radiopaque layer and a non-radiopaque polymer layer. In such embodiments, the radiopaque layer includes the radiopaque bioceramic particles. The non-radiopaque layer is free or substantially free of radiopaque particles. "Substantially free" can refer to a concentration of radiopaque bioceramic particles of less than 1 vol % or a concentration insufficient to make the stent fluoroscopically visible. In these embodiments, the radiopaque layer can be an abluminal layer, luminal layer, or a layer between a luminal and abluminal layer.

In some embodiments, the radiopaque layer can include radiopaque bioceramic particles mixed or dispersed in a matrix polymer. The matrix polymer can be the same or different from the polymer of the non-radiopaque layer. In other embodiments, the radiopaque layer can include a composition including the radiopaque bioceramic particles with grafted polymers without a blended matrix polymer.

Exemplary embodiments can include a non-radiopaque layer formed from a semi-crystalline polymer with a Tg above body temperature such as PLLA or PLGA. In exemplary embodiments, the matrix polymer of the radiopaque layer can also be a semi-crystalline polymer such as PLLA or PLGA. Alternatively, the matrix polymer of the radiopaque layer can be an elastomeric polymer or contain elastomeric segments, for example, PCL, PDO, PLLA-co-PCL, PLLA-b-PCL. Such elastomeric polymers or segments can have a Tg below body temperature. The grafted polymers of bioceramic particles with such grafted polymers can also be these two exemplary set of embodiments.

In certain embodiments, the non-radiopaque layer may be primarily or completely responsible for providing mechanical support and maintaining patency of vessel. In such embodiments, the concentration of the radiopaque bioceramic particles in the radiopaque layer can be less than 5%, 5-10%, 10-20%, 20-30%, or greater than 30% by volume. In embodiments in which the radiopaque layer is not required or is only partially required to provide support, the concentration of the radiopaque bioceramic particles may be at a level that mechanical properties are adversely affected by the particles.

In other embodiments, the radiopaque layer can assist the support layer in maintaining patency. In such embodiments, the concentration of bioceramic particles can be limited so the mechanical properties of the stent body are not adversely affected.

Figure 5A:
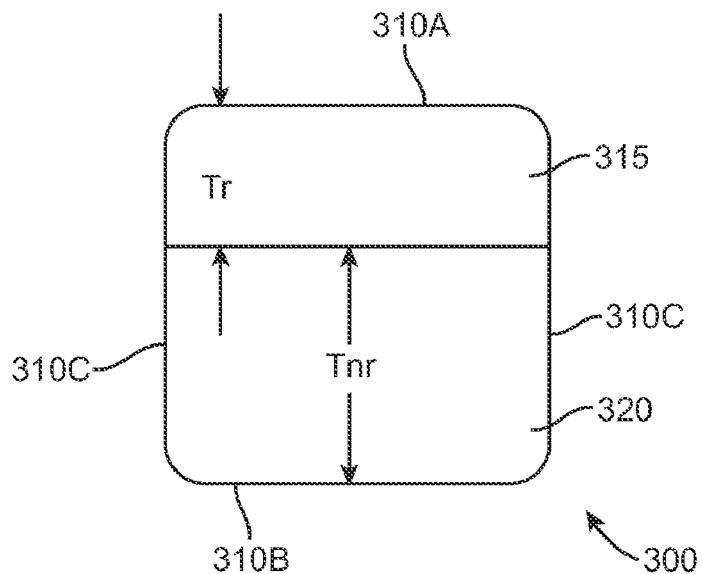
FIG. 5A-B depict cross-section of a structural element with a radiopaque layer and a non-radiopaque layer.
Figure 5B:
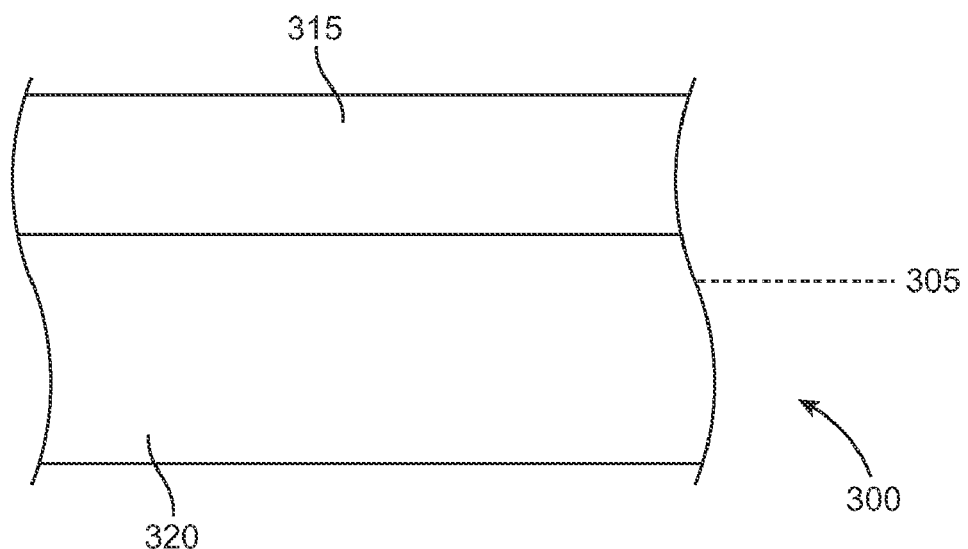

Various structural embodiments of a stent body with a radiopaque layer are contemplated and are described and illustrated herein. FIGS. 5A-B illustrate an exemplary embodiment of a strut or structural element 300 of a stent scaffolding with a radiopaque layer. FIG. 5A depicts a cross-section orthogonal to a longitudinal axis 305 of structural element 300 with an abluminal surface 310A, a luminal surface 310B, and sidewall surfaces 310C. FIG. 5B depicts an axial cross-section of structural element 300. Structural element 300 has a radiopaque layer 315 disposed over and in contact with a non-radiopaque layer 320. In other embodiments, one or more layers can be disposed between radiopaque layer 315 and non-radiopaque layer 320. As shown, radiopaque layer 315 is an abluminal layer, however, in alternative embodiments, radiopaque layer 315 can be a luminal layer.

As shown in FIGS. 5A-B, radiopaque layer 315 has a radial thickness Tr and non-radiopaque layer 320 has a radial thickness (Tnr). In some embodiments, the radial thickness of the radiopaque layer can be adjusted to provide a desired degree of fluoroscopic visibility. Additionally, the thickness of the non-radiopaque layer can be adjusted so that the stent maintains a desired degree of patency of a lumen, such as, less than 50%, 50-60%, 60-80%, or greater than 80% of the deployed diameter of the stent. In exemplary embodiments, the thickness of a radiopaque layer can be less than 10 µm, 10-30 µm, or greater than 30 µm. Also, in exemplary embodiments, the non-radiopaque layer is less than 2, 2-5, or more than 5 times thicker than the radiopaque layer.

As indicated above, a stent body or scaffolding can be formed by cutting a stent pattern into a tube. In certain embodiments, a stent with a radiopaque layer and a non-radiopaque layer can be fabricated from a tube having such layers. As described in more detail below, such a tube can be formed by co-extrusion. In such embodiments, a stent pattern is cut into the layered tube to form a stent scaffolding. The stent scaffolding can include a non-radiopaque layer formed from the tube non-radiopaque layer and a radiopaque layer formed from the tube radiopaque layer.

Figure 6A:
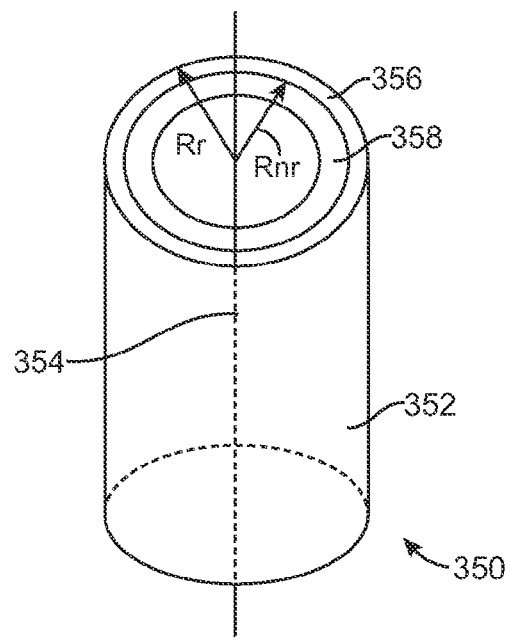
FIG. 6A depicts a perspective view of a tube with wall composed of two layers.
Figure 6B:
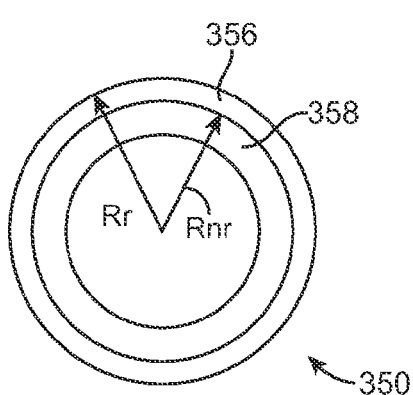
FIG. 6B depicts a radial cross-section the tube of FIG. 6A.
Figure 6C:
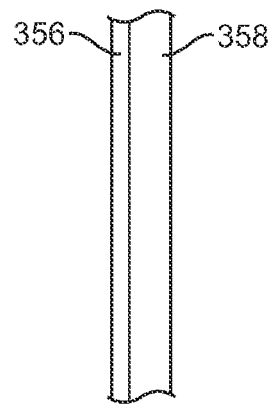
FIG. 6C depicts a cross-section of the wall of the tube of FIG. 6A.

FIG. 6A depicts a perspective view of a tube 350 with an outer surface 352 and a cylindrical axis 354. The wall of tube 350 has two concentric or substantially concentric layers, an outer layer 356 and an inner layer 358. Outer layer 356, which has an outer radius, Rr, is a radiopaque layer and inner layer 358 is a non-radiopaque layer with a thickness Rnr. FIG. 6B depicts a radial cross-section of tube 350 and FIG. 6C depicts a cross-section of the wall of tube 350 parallel to axis 354 of tube 350.

Figure 7:
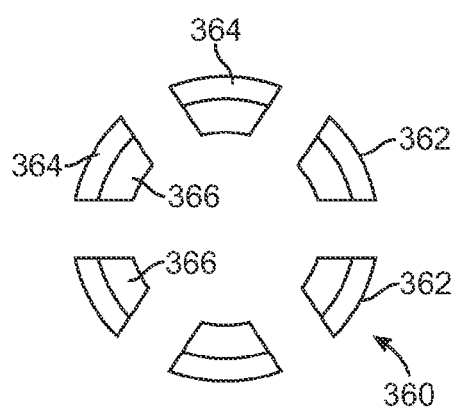
FIG. 7 depicts a radial cross-section of a stent scaffolding cut from the tube of FIG. 6A.

FIG. 7 depicts a radial cross-section of a stent scaffolding 360 cut from tube 350. Stent scaffolding 360 has structural elements 362 which have an abluminal radiopaque layer 364 and a luminal non-radiopaque layer 366. Radiopaque layer 364 is formed from outer layer 356 of tube 350 and a non-radiopaque layer 366 formed from inner layer 358 of tube 350. In further embodiments, a stent scaffolding having more than two layers can be formed from a tube having more than two radial layers.

In certain embodiments, a tube with a radiopaque layer and a non-radiopaque layer can be formed by co-extrusion. In such embodiments, a tube can be co-extruded to have a radiopaque layer and a non-radiopaque layer.

An extruder generally includes a barrel through which a polymer melt is conveyed from an entrance to an exit port. The polymer can be fed to the extruder barrel as a melt or in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is mixed, for example, through the use of rotating screws.

In certain embodiments, the extrudate for forming a radiopaque layer can include a polymer melt mixed with radiopaque bioceramic particles. In some embodiments, the mixture can be formed first and then fed to an extruder for forming the layered tubing. In other embodiments, the polymer and radiopaque polymer can be fed separately to the extruder and mixed or compounded within the extruder. In one embodiment, the extrudate for forming the radiopaque layer can include bioceramic particles with grafted polymers without a matrix polymer.

The polymer melt exits the extruder to a die placed at the end of the extruder barrel. A die generally refers to a device having an orifice with a specific shape or design geometry that it imparts a shape to a polymer melt pumped from an extruder. In the case of tubing extrusion, the die has a circular shaped orifice that imparts a cylindrical shape to the polymer melt exiting the die. The function of the die is to control the shape of the polymer melt by delivering polymer melt to the orifice. The polymer melt can be delivered at a constant rate, temperature, and pressure.

Co-extrusion refers to the process of extruding two or more materials through a single die with two or more orifices arranged so that the extrudates from the separate orifices merge and weld together into a laminar structure before cooling or chilling. Each material can be fed to the die from a separate extruder, but the orifices may be arranged so that each extruder supplies two or more layers of the same material. In the case of tubing co-extrusion, the die can include concentric circular slits through which the different materials exit to form a tube with two or more layers.

Figure 8:
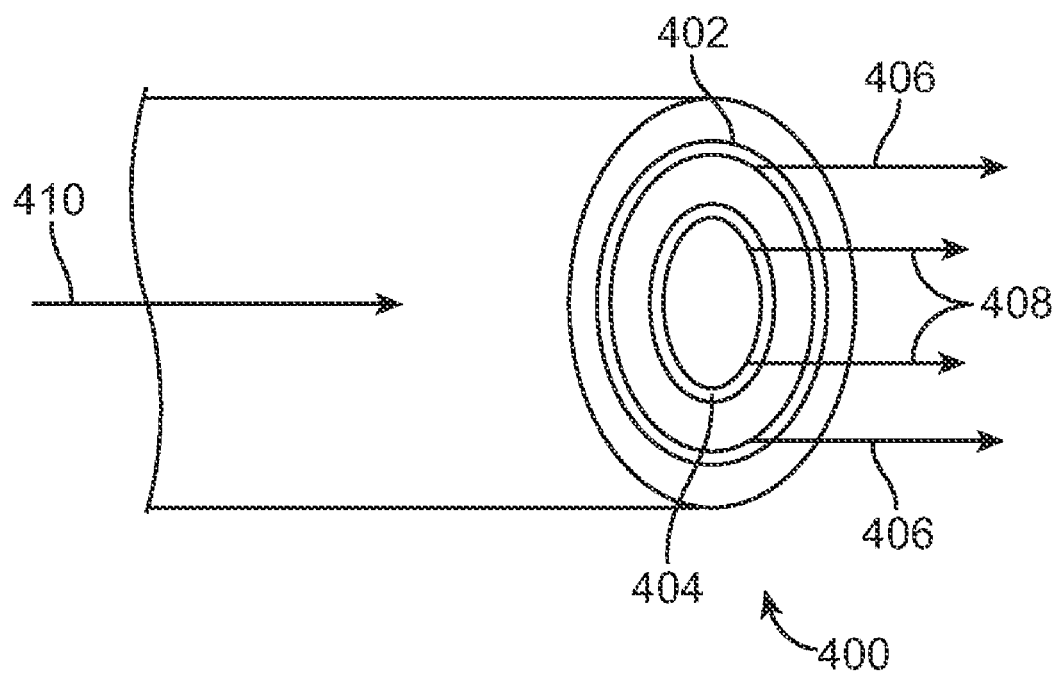
FIG. 8 depicts a die having two circular orifices.

In some embodiments of the present invention, an extrudate including radiopaque bioceramic particles is formed in one extruder and fed to a die with two or more circular orifices for formation of a layered tube. In an exemplary embodiment, FIG. 8 depicts a die 400 having two circular orifices, an outer orifice 402 and an inner orifice 404. An extrudate including bioceramic particles and polymer material can exit through outer orifice 402, as shown by arrows 406, while an extrudate corresponding to a non-radiopaque layer can exit through inner orifice 404, as shown by arrows 408. The extrudates are conveyed through die 400, in the direction of an arrow 410. The exiting extrudates merge and are welded together to form a cylindrical layered film which is cooled to form a tube.

In other embodiments, a layered tube including a radiopaque layer can be fabricated by forming a coating the layer over a surface of a tube. The coating can be formed over the inner surface, the outer surface, or both. The coating can include radiopaque bioceramic particles and polymer. The tube can be formed from a polymer with no radiopaque materials embedded within. A stent pattern can then be cut into the coated tube to form a stent scaffolding with a radiopaque layer and a non-radiopaque layer.

In such embodiments, a coating material may be applied to the tube by methods known in the art such as by spraying or dipping. The coating material can be a solution including a polymer dissolved in a solvent. The coating material can further include radiopaque bioceramic particles suspended in the solvent. In some embodiments, the coating material includes bioceramic particles with grafted polymer, the grafted polymer being dissolved in the solvent. In some embodiments, the polymer solution can also include a drug dispersed in the solution to allow the radiopaque layer to serve as a therapeutic layer. The coating material may be applied to the stent by immersing the stent in the coating material, by spraying the material onto the stent, drop coating, or by other methods known in the art. The solvent in the solution is then removed, for example, by evaporation, leaving on the stent surfaces a polymer coating with bioceramic particles and polymer and in some embodiments, a drug.

Further embodiments of the present invention can include a stent with two or more radiopaque layers. Additional embodiments of the stent can also include two or more non-radiopaque layers. Embodiments of such stents can be fabricated by methods described above. In particular, a tube having the selected number of layers can be formed through co-extrusion and a stent fabricated therefrom.

In the third set of embodiments, a stent can have a radiopaque coating over a portion or all of a surface of a stent body or scaffolding or a structural element of a stent body or scaffolding. In such embodiments, the stent body or scaffolding can be formed of a polymer having no or substantially no bioceramic particles. In other embodiments, the stent body or scaffolding can be formed of bioceramic particles mixed with a polymer. The concentration of particles in the scaffolding (e.g., less than 5 vol %, or 5-10 vol %) may be less than the concentration of particles in the coating (e.g., 10-20 vol %, or greater than 20%). The scaffolding can be a semi-crystalline polymer with a Tg above body temperature.

In some embodiments, the radiopaque coating can include radiopaque bioceramic particles mixed or dispersed in a matrix polymer. The matrix polymer can be the same or different from the polymer of the stent body or scaffolding. In other embodiments, the radiopaque coating can include a composition including the radiopaque bioceramic particles with grafted polymers without a blended matrix polymer.

Exemplary embodiments can include a stent body formed from a semi-crystalline polymer with a Tg above body temperature such as PLLA or PLGA. In exemplary embodiments, the matrix polymer of the coating layer can also be a semi-crystalline polymer such as PLLA or PLGA. Alternatively, the matrix polymer of the coating layer can be an elastomeric polymer or contain elastomeric segments, for example, PCL, PDO, PLLA-co-PCL, PLLA-b-PCL. Such elastomeric polymers or segments can have a Tg below body temperature. The grafted polymers of bioceramic particles with such grafted polymers can also be these two exemplary set of embodiments.

In some embodiments, the concentration of the radiopaque bioceramic particles in the radiopaque layer can be less than 5%, 5-10%, 10-20%, 20-30%, or greater than 30% by volume. Since the radiopaque coating is not required to provide support, in some embodiments, the concentration of the radiopaque material can be increased without regard to the adverse effect of a high concentration of bioceramic particles on mechanical properties of the layer.

Figure 9A:
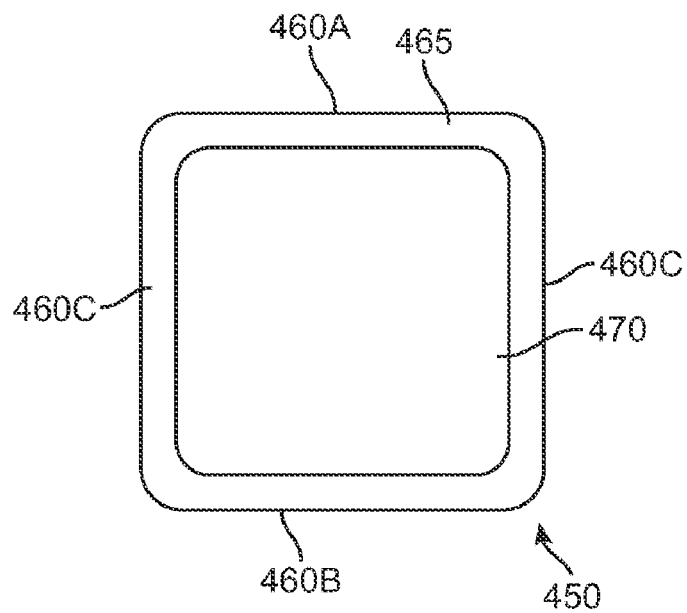
FIGS. 9A-B depict cross-sections of a structural element of a stent with a radiopaque coating layer over a body portion.
Figure 9B:
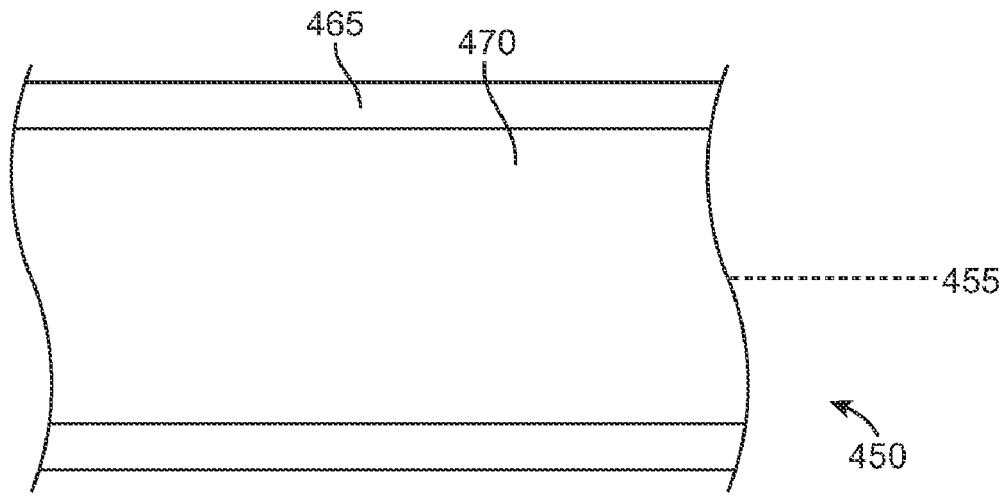

FIG. 9A depicts a cross-section orthogonal to a longitudinal axis 455 of structural element 450 with an abluminal surface 460A, a luminal surface 460B, and sidewall surfaces 460C. FIG. 9B depicts an axial cross-section of structural element 450. Structural element 450 includes a body portion 470 with a radiopaque coating layer 465 disposed over and in contact with body portion 470. As shown, radiopaque coating layer 465 is disposed over the whole perimeter of body portion 470. In other embodiments, a radiopaque coating layer can be selectively disposed over the abluminal layer, luminal layer, or both.

In some embodiments, a drug can be included in a radiopaque coating layer. Alternatively or additionally, a drug-containing layer can be disposed above the radiopaque layer or between the radiopaque layer and the body portion.

Furthermore, the radiopaque coating layer can be formed by applying a coating material a body or scaffolding. As described above, the coating material may be applied to the stent by methods known in the art such as by spraying or dipping. The coating material can be a solution including a polymer dissolved in a solvent. The coating material can further include radiopaque bioceramic particles suspended in the solvent. In some embodiments, the coating material includes bioceramic particles with grafted polymer, the grafted polymer being dissolved in the solvent. In some embodiments, the polymer solution can also include a drug dispersed in the solution. The coating material may be applied to the stent by immersing the stent in the coating material, by spraying the material onto the stent, drop coating, or by other methods known in the art. The solvent in the solution is then removed, for example, by evaporation, leaving on the stent surfaces a radiopaque coating layer.

Bioceramics can include any ceramic material that is compatible with the human body with reactive hydroxyl or amine groups. More generally, bioceramic materials can include any type of compatible inorganic material or inorganic/organic hybrid material with reactive hydroxyl or amine groups. Bioceramic materials can include, but are not limited to, alumina, zirconia, apatites, calcium phosphates, silica based glasses, or glass ceramics, and pyrolytic carbons. Bioceramic materials can be bioabsorbable and/or active. A bioceramic is active if it actively takes part in physiological processes. A bioceramic material can also be "inert," meaning that the material does not absorb or degrade under physiological conditions of the human body and does not actively take part in physiological processes.

Illustrative examples of apatites and other calcium phosphates, include, but are not limited hydroxylapatite ($Ca_{10}(PO_4)_6(OH)_2$), floroapatite ($Ca_{10}(PO_4)_6F_2$), carbonate apatide ($Ca_{10}(PO_4)_6CO_3$), tricalcium phosphate ($Ca_3(PO_4)_2$), octacalcium phosphate ($Ca_8H_2(PO_4)_6\text{-}5H_2O$), octacalcium phosphate ($Ca_8H_2(PO_4)6\text{-}5H_2O$), calcium pyrophosphate ($Ca_2P_2O_7\text{-}2H_2O$), tetracalcium phosphate ($Ca_4P_2O_9$), and dicalcium phosphate dehydrate ($CaHPO_4\text{-}2H_2O$).

The term bioceramics can also include bioactive glasses that are bioactive glass ceramics composed of compounds such as $SiO_2$, $Na_2O$, $CaO$, and $P_2O_5$. For example, a commercially available bioactive glass, Bioglass®, is derived from certain compositions of $SiO_2$—$Na2O$—$K_2O$—$CaO$—$MgO$—$P_2O_5$ systems. Some commercially available bioactive glasses include, but are not limited to:

45S5: 46.1 mol % SiO2, 26.9 mol % CaO, 24.4 mol % $Na_2O$ and 2.5 mol % $P_2O_5$;

58S: 60 mol % SiO2, 36 mol % CaO, and 4 mol % $P_2O_5$; and

S70C30: 70 mol % SiO2, 30 mol % CaO.

Another commercially available glass ceramic is A/W.

Various sizes of the bioceramic particles may be used in the composite. For example, the bioceramic particles can include, but are not limited to, nanoparticles and/or micro particles. A nanoparticle refers to a particle with a characteristic length (e.g., diameter) in the range of about 1 nm to about 1,000 nm. A micro particle refers to a particle with a characteristic length in the range of greater than 1,000 nm and less than about 10 micrometers. Additionally, bioceramic particles can be of various shapes, including but not limited to, spheres and fibers.

In some embodiments, bioceramic particles may include an adhesion promoter to improve the adhesion between the particles and the polymer matrix. In one embodiment, an adhesion promoter can include a coupling agent. A coupling agent refers to a chemical substance capable of reacting with both the bioceramic particle and the polymer matrix of the composite material. A coupling agent acts as an interface between the polymer and the bioceramic particle to form a chemical bridge between the two to enhance adhesion.

The adhesion promoter may include, but is not limited to, silane and non-silane coupling agents. For example, the adhesion promoter may include 3-aminopropyltrimethoxysilane, 3-aminopropyltriethoxysilane, aminopropylmethyldiethoxy silane, organotrialkoxysilanes, titanates, zirconates, and organic acid-chromium chloride coordination complexes. In particular, 3-aminopropyltrimethoxysilane has been shown to facilitate adhesion between poly(L-lactide) and bioglass. Biomaterials 25 (2004) 2489-2500.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly (caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

For the purposes of the present invention, the following terms and definitions apply:

The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

"Solvent" is defined as a substance capable of dissolving or dispersing one or more other substances or capable of at least partially dissolving or dispersing the substance(s) to form a uniformly dispersed solution at the molecular- or ionic-size level. The solvent should be capable of dissolving at least 0.1 mg of the polymer in 1 ml of the solvent, and more narrowly 0.5 mg in 1 ml at ambient temperature and ambient pressure.

The examples and experimental data set forth below are for illustrative purposes only and are in no way meant to limit the invention. The following examples are given to aid in understanding the invention, but it is to be understood that the invention is not limited to the particular materials or procedures of examples.

EXAMPLES

Example 1

Preparation of Radiopaque Hydroxylapatite Nano Particles

Step 1: 10 g hydroxylapatite, 100 ml chloroform, 40 g triiodobenzoyl chloride and 20 ml of triethyl amine are added into a 500 ml three neck glass bottle to form a reaction solution. The reaction solution stirred for 4 h to finish the esterification reaction.

Step 2: Centrifuge the formed radiopaque hydroxylapatite nano particles from the reaction solution at 5000 rpm for 20 min.

Step 3: Add 100 ml chloroform into the obtained radiopaque hydroxylapatite nano particles, stir 10 min, and then centrifuge again to get purified final product.

Step 4: Dry final product at 70° C. in a vacuum oven till constant weight.

Example 2

Stent Preparation from a Blend of PLLA/Radiopaque Hydroxylapatite Nano Particles of Example 1

Step 1: A tubing is formed through the extrusion of the blend of PLLA/radiopaque hydroxylapatite nano particles (80:20 by volume). The inside diameter (ID) and outside diameter (OD) of the extruded tubing are set to 0.02 inch and 0.08 inch.

Step 2: Radially expand the extruded tubing and cut a stent pattern in the tubing with a laser.

Example 3

Stent Preparation from a Blend of PLLA/Radiopaque Hydroxylapatite Nano Particles of Example 1 Through Co-Extrusion Step 1: A two-layer tubing is formed through the co-extrusion of PLLA as an inner layer and a blend of PLLA-co-PCL/radiopaque hydroxylapatite nano particles (70:30 by volume) as an outer layer. The thickness of the inner layer and the radiopaque outer layer is set to 0.05 inch and 0.02 inch, respectively. The ID and OD of the extruded tubing are set to 0.02 inch and 0.09 inch.

Step 2: Radially expand the extruded tubing and cut a stent pattern in the tubing with a laser.

Example 4

Preparation of Radiopaque Hydroxylapatite Particles with Grafted PLLA Chain Containing Radiopaque End Groups Step 1: 10 g nano hydroxylapatite, 0.01 g stannous octoate catalyst, 5 g L-lactide (LLA) are added into a reactor with 50 ml xylene. Allow the reaction to proceed for 48 h at 120° C. Then cool down to room temperature.

Step 2: Add 20 g triiodobenzoyl chloride and 10 ml of triethyl amine and stir the solution for 4 h to finish the esterification reaction.

Step 3: Precipitate the final product into 400 ml methanol and dry the final product in a vacuum oven till constant weight.

Example 5

Preparation of Radiopaque Hydroxylapatite Particles Grafted with PCL-co-PLLA Chain Containing Radiopaque End Groups and Side Groups Step 1: 10 g nano hydroxylapatite particles, 0.01 g stannous octoate catalyst, 2.5 g caprolactone (CL) and 50 ml xylene are added into a reactor free of moisture and oxygen. Allow the reaction to proceed for 24 h h at 120° C.

Step 2: Add 2.5 g LLA and allow the reaction to proceed for another 24 h.

Step 3: Add 10 ml of triethyl amine and 20 g triiodobenzoyl chloride and stir for 4 h to finish the esterification reaction.

Step 4: Precipitate the final product into 400 ml methanol and dry the final product in a vacuum oven till constant weight.

Step 5: Mix 10 g product having radiopaque end groups made in step 4 with 50 ml lithium diisopropyl amide solution in THF (2M/L). Stir the mixture for 1 h.

Step 6: 15 g iodine (in 20 ml THF) is added into the reactor and the mixture is stirred for 2 h.

Step 7: The final product with formed iodine side groups along the PCL block backbone is precipitated into 300 ml methanol, filtered out, and dried under vacuum at 80° C. till constant weight.

Example 6

Stent Preparation from a Blend of PLLA/Radiopaque Hydroxylapatite Nano Particles of Examples 4 or 5

Step 1: A tubing is formed through the extrusion of a blend of PLLA/radiopaque hydroxylapatite nano particles (80:20 by volume). The ID and OD of the extruded tubing are set to about 0.02 inch and 0.08 inch, respectively.

Step 2: Radially expand the extruded tubing and cut a stent pattern in the tubing with a laser.

Example 7

Stent Preparation from a Blend of PLLA/Radiopaque Hydroxylapatite Nano Particles of Examples 4 or 5 Through Co-Extrusion Step 1: A two-layer tubing is formed through the co-extrusion of PLLA as an inner layer and a blend of PLLA-co-PCL/radiopaque hydroxylapatite nano particles (60:40 by volume) as an outer layer. The thickness of the inner layer and the radiopaque outer layer is set to 0.05 inch and 0.02 inch, respectively. The ID of the extruded tubing is set to about 0.02 inch and the OD is about 0.09 inch.

Step 2: Radially expand the extruded tubing and cut a stent pattern in the tubing with a laser.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent formed at least in part from a bioceramic/polymer composite, the composite having a plurality of bioceramic particles dispersed within a matrix polymer, wherein the bioceramic particles comprise radiopaque functional groups grafted to a surface of the bioceramic particles, wherein the radiopaque functional groups allow the stent to be fluoroscopically visible, wherein the radiopaque functional groups are chemically bonded to reactive groups including hydroxyl groups on the ceramic surface of the bioceramic particles.

2. The stent of claim 1, wherein the radiopaque functional groups are selected from the group consisting of iodine, triiodobenzoyl chloride, and triiodobenzoic acid, wherein the radiopaque functional groups are grafted to the surface of the bioceramic particles by an esterification reaction of hydroxyl groups of the bioceramic particles with the radiopaque functional groups.

3. The stent of claim 1, wherein the matrix polymer is biodegradable.

4. The stent of claim 1, wherein the matrix polymer is selected from the group consisting of PLLA, PLGA, PDLA, PCL, PGA, PLLA-co-PCL, biodegradable polyurethanes, poly(ester amides), polyanhydrides, and polycarbonates.

5. The stent of claim 1, wherein the bioceramic particles are selected from the group consisting of hydroxylapatite and calcium sulfate.

6. The stent of claim 1, wherein the stent comprises a stent body including a radiopaque layer comprising the composite and a non-radiopaque layer, the radiopaque layer being an abluminal layer or a luminal layer.

7. The stent of claim 1, wherein the stent comprises a scaffolding with a coating disposed above the scaffolding surface, the coating comprising the composite.

8. The stent of claim 1, wherein the stent comprises a scaffolding formed from the composite.

* * * * *